United States Patent [19]

Harman

[11] 4,451,253

[45] May 29, 1984

[54] MEANS AND METHOD FOR ADMINISTERING MEDICINALS

[76] Inventor: Sherman M. Harman, 9302 Michaels Way, Ellicott City, Md. 21043

[21] Appl. No.: 427,136

[22] Filed: Sep. 29, 1982

Related U.S. Application Data

[63] Continuation-in-part of Ser. No. 217,780, Dec. 18, 1980, abandoned.

[51] Int. Cl.³ .............................................. A61M 5/18
[52] U.S. Cl. ...................................................... 604/60
[58] Field of Search ...................... 604/60, 61, 59, 57, 604/48

[56] References Cited

U.S. PATENT DOCUMENTS

| | | | |
|---|---|---|---|
| 2,502,909 | 4/1950 | Wick et al. | 604/60 |
| 2,513,014 | 6/1950 | Fields | 604/60 |
| 2,601,852 | 7/1952 | Wendt | 604/59 |
| 2,761,446 | 9/1956 | Reed | 604/59 |
| 3,744,493 | 7/1973 | Booher et al. | 604/60 |
| 4,105,030 | 8/1978 | Kercso | 604/61 |
| 4,223,674 | 9/1980 | Fluent et al. | 604/61 |

*Primary Examiner*—John D. Yasko

*Attorney, Agent, or Firm*—Charles E. Temko

[57] ABSTRACT

A device for administering elongate medicinal pellets in subcutaneous applications. The device includes a hand-held guide element including a hollow barrel enclosing a sliding member having a needle locking means at one end thereof. A disposable cartridge element includes a hollow needle containing a pellet to be implanted and an obturator of length somewhat greater than that of the needle. In use, the cartridge element is engaged at an end thereof with the guide element. The free end of the needle is inserted into the subcutaneous fat of the patient, and the sliding member is moved in an opposite direction to withdraw the needle into the hollow barrel. During this movement, the obturator is maintained relatively stationary by engaging an abutment on the guide element, at one end thereof, the opposite end of the obturator engaging an end of the pellet, so that as the needle is withdrawn, the pellet remains in implanted position. A composite pellet having a core formed of a first ingredient, and a surrounding sleeve formed of a second ingredient is also disclosed, as is a method for making the pellets using a soluble inert core having first and second ingredients coated thereon.

3 Claims, 8 Drawing Figures

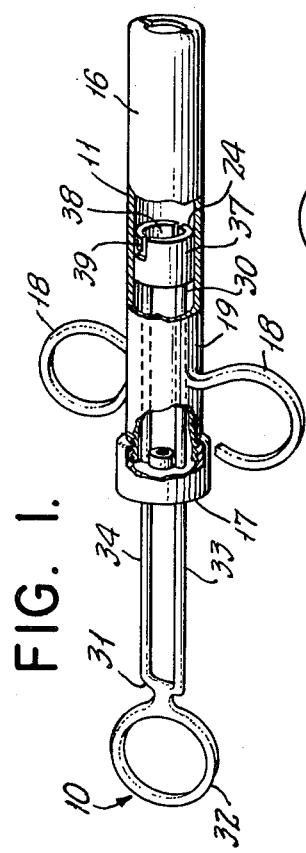
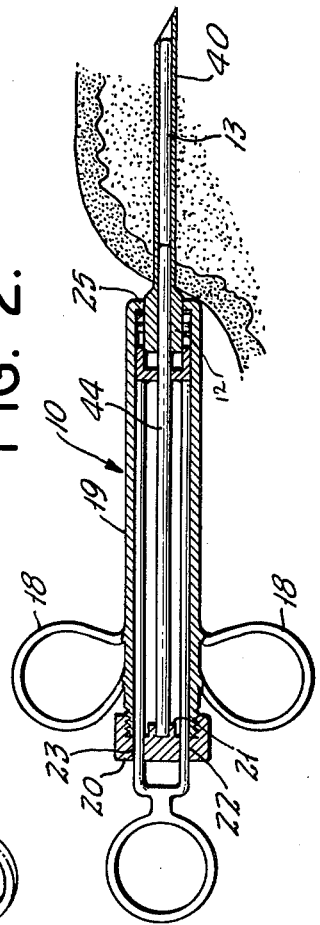
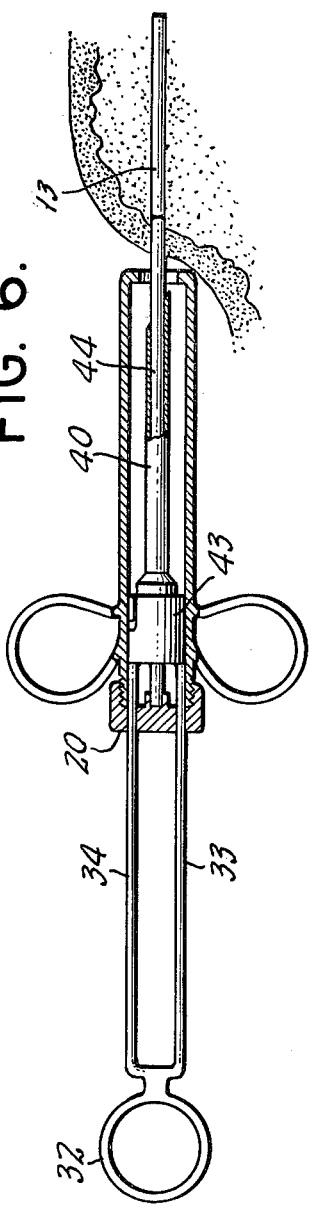
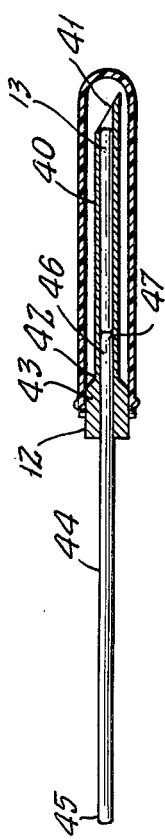

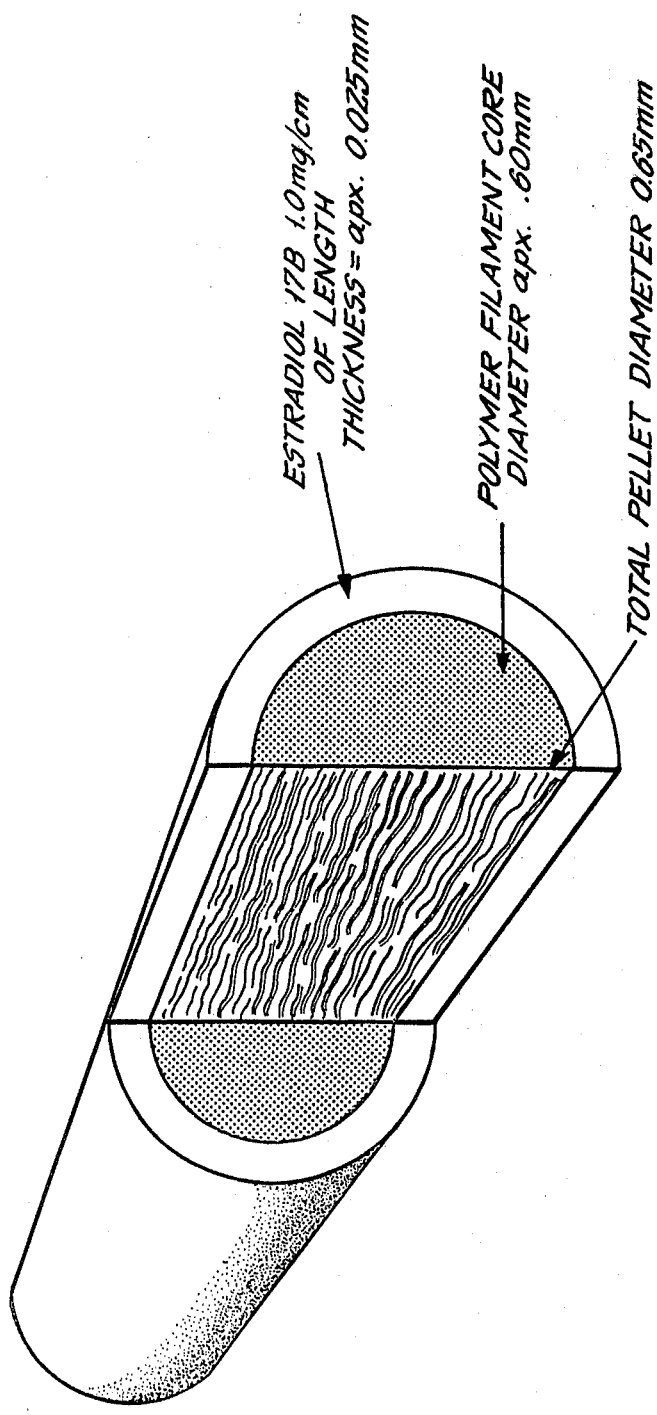

MEANS AND METHOD FOR ADMINISTERING MEDICINALS

RELATED APPLICATION

This application is a continuation in part of my co-pending application, Ser. No. 217,780, filed Dec. 18, 1980, now abandoned under the title MEANS AND METHOD FOR ADMINISTERING MEDICINALS.

BACKGROUND OF THE INVENTION

This invention relates generally to the field of surgical instrumentation, and more particularly to an improved means and method for administering certain solid form medicaments in subcutaneous applications, as well as the manufacture of the medicaments themselves.

While most subcutaneous applications involve the use of a liquid medicament injected through a syringe, some treatments require the introduction of small amounts of medicament into the bloodstream on a substantially continuous basis over an extended period of time. This requirement is best fulfilled by the use of a medicament in solid pellet form, the exposed surfaces of which continuously dissolve into the bloodstream.

A typical example of this procedure is the treatment of menopausal estrogen deficiency in women using 17 beta-estradiol pellet implants. Such replacement has a number of important salutory effects. In the known method, the implanted dose is in the form of compressed, cylindrical pellets containing 25 mg. of 17 beta-estradiol without excipient. The pellets measure approximately 3.2 mm. in diameter and are 3.5 mm. long. Implantation is effected using a cannula with the same inside diameter as that of the pellet (3.2 mm.) and provided with two trocars. A first trocar is pointed for introducing the cannula, and a second trocar is blunt for inserting the pellet thereafter. After a small quantity of local anesthesia has been injected intra and subcutaneously, a small incision is made through the skin with a pointed scalpel blade. Through this incision the cannula with the pointed trocar is inserted several cm. into the subcutaneous fat, and nearly parallel to the skin, after which the implant pellet is inserted into the cannula and pushed therethrough using the blunt trocar, following which the cannula is withdrawn. One or two sutures may be required to close the incision. While a skilled physician can often complete the procedure in a few minutes, the cannula and the trocars must be sterilized for each use, and the procedure can hardly be considered convenient. Furthermore the known pellet is of such a size that the continued administration of estrogen lasts approximately three months.

There is considerable medical authority to the effect that optimum treatment for women who require estrogen replacement therapy is by administering small daily doses of estradiol for three to four weeks followed by five or seven days off, with the addition of a small dose of an "opposing" progestin during the last ten to twelve days of the estrogen treatment, at present, following the use of oral medication. It is increasingly apparent from well-conducted medical research that the oral route exposes the liver to unphysiologically high doses of estrogen, resulting in altered liver protein synthesis and increased risks of various untoward effects including: high blood pressure, increased clotting of blood (phlebitis, lung clots, and cerebral clots), altered blood lipids (possible increased risk of coronary artery disease), and benign vascular tumors of the liver itself (which may rupture and bleed).

As detailed above, the alternative parenteral method for supplying estrogen directly to the systemic circulation results in prolonged exposure to unopposed and continuous estrogen. Such unopposed and continuous exposure to estrogens, by either the oral or parenteral route, has been shown to result in an increased risk of uterine cancer. Therefore the ideal method would use a small pellet, lasting only three-four weeks, provide for progestin administration to mature the uterine lining, and be convenient and painless enough that monthly repetition would be feasible for most patients. The other parenteral alternative, utilizing intramuscular injection of estradiol in oil, results in transient very high estrogen levels, slowly decreasing in an unpredictable fashion, and is painful. The invention described herein is designed to overcome the objections and side effects of such replacement therapy.

Devices for implanting pellets subcutaneously are known in veterinary medicine. One such device is disclosed in the patent to Kercso, U.S. Pat. No. 4,105,030, of Aug. 8, 1978. Another is disclosed in the patent to Fluent et al., U.S. Pat. No. 4,223,674, of Sept. 23, 1980. While not without utility in the field of veterinary medicine, such devices are not suitable for use with human patients. The devices disclosed in these patents contemplate the use of needles varying in diameter from 2.7 to 4.0 mm., and 80 to 90 mm. in length. Such large needles would be unacceptably painful for routine use in humans. On the other hand, neither of the prior art devices is equipped to handle a fine disposable needle. The ram rod or obturator part of these devices would not fit into a fine needle, nor would the complex mechanisms for withdrawing the needles function correctly with a fine obturator without bending or breaking the needle.

More importantly, the prior art devices contemplate a pellet size of 2.5 to 3.5 mm. in diameter. Implanting pellets of such size calls for the creation of an unacceptably large wound in the patient.

Most importantly, neither of the prior art devices can be used in a manner sufficiently sterile for human purposes. In the Kercso device, there is a front needle guide which actually comes in contact with the barrel of the needle prior to administration. In the Fluent et al. device, there is a requirement for the passage of a "locking nut" over the barrel of the needle, with each change, thus risking contamination each time the needle is changed. Although both disclosures mention the use of a cartridge, neither teaches the construction of a unit containing needle, pellet, and sterile disposable obturator. Fluent et al requires the pressing of the instrument against the patient to initiate the withdrawal of the needle, an action which is not possible with human patients. Kercso provided for the withdrawal of the needle under the action of a spring, a process also suitable only for use in veterinary medicine. Neither disclosure shows a device suitable for human use.

SUMMARY OF THE INVENTION

Briefly stated, the invention contemplates the provision of an improved device for the subcutaneous implantation of a solid elongated composite pellet in a manner somewhat resembling the administration of a liquid drug using a conventional hypodermic syringe. The device includes a hollow cylinder slidably mounting a pair of arms having a cartridge engaging terminal at a distal end thereof. A disposable sealed, pre-sterilized cartridge element includes a hollow needle with means at the base or hub thereof for engaging said terminal. A pellet of cylindrical configuration is positioned in the needle, and a blunt obturator extends through the base of the needle. After subcutaneous insertion, the guide arms are moved outwardly within the cylinder to result in the withdrawal of the needle. The obturator remains fixed, and maintains the pellet in implanted position as it is uncovered by withdrawal of the needle. Following implantation of the pellet, the cartridge element is discarded. The pellet may be of either of two types. A pure estradiol pellet delivers estrogen only which may be supplemented at the end of a cycle by orally administering progestin. A second type contains a 0.2 mm. core of progesterone estradiol mixture to release progestin during the last one third of the cycle. The exact size and proportional mix of the core may be varied to suit specific requirements.

In a preferred method of pellet fabrication, the most convenient configuration is that including a core of biologically inert biodegradable polymer such as polyglactin, polylactone, polylactide, etc., which are materials from which synthetic absorbable sutures are currently manufactured, the core being coated with a thin layer of active medication, such as estrogen, estrogen-progestogen, hormone antagonist, or other drugs described in my copending application. Pellets will, in general, be from 15 to 25 mm. long, and of diameter ranging from 0.04 to 0.068 mm. Pellet fabrication may be by a number of methods. The fiber core may be coated by dipping it in an estradiol melt and drawing it through a die while still hot to fix the outer diameter; by repeated dipping in a solution of estradiol and volatile solvent to build up a coat of the desired thickness; or by spray coating estradiol in a volatile solvent onto a rotating fiber with a fine spray under pressure.

The advantages of using a coated inert fiber core are ease of fabrication of a "layered" pellet by dipping in or spraying in sequential coats of solutions of various compositions, and the fact that the surface area available for absorption changes very little, in the order of less than ten percent, from onset of absorption to complete dissolution of the drug, which provides a nearly constant rate of medication delivery for the entire duration of the action of the pellet, as well as a rapid cut-off of action at the end.

BRIEF DESCRIPTION OF THE DRAWINGS

In the drawings, to which reference will be made in the specification, similar reference characters have been employed to designate corresponding parts throughout the several views.

FIG. 1 is a perspective side view, partly broken away to show details of an embodiment of the invention, with a disposable needle cartridge removed.

FIG. 2 is a central longitudinal sectional view thereof with the needle cartridge attached, wherein the apparatus is in the "ready" or pre-injection configuration.

FIG. 3 is a central sectional view of a needle cartridge element in detached condition.

FIG. 4 is a central longitudinal sectional view of a pellet element.

FIG. 5 is a an end elevational view of the pellet element shown in FIG. 4.

FIG. 6 is a central longitudinal sectional view thereof, with needle cartridge attached, and showing the device in "discharged" or post-injection configuration.

FIG. 7 is a schematic perspective, partially in section of a first alternate form of pellet.

DETAILED DESCRIPTION OF THE DISCLOSED EMBODIMENT

Figure 8:
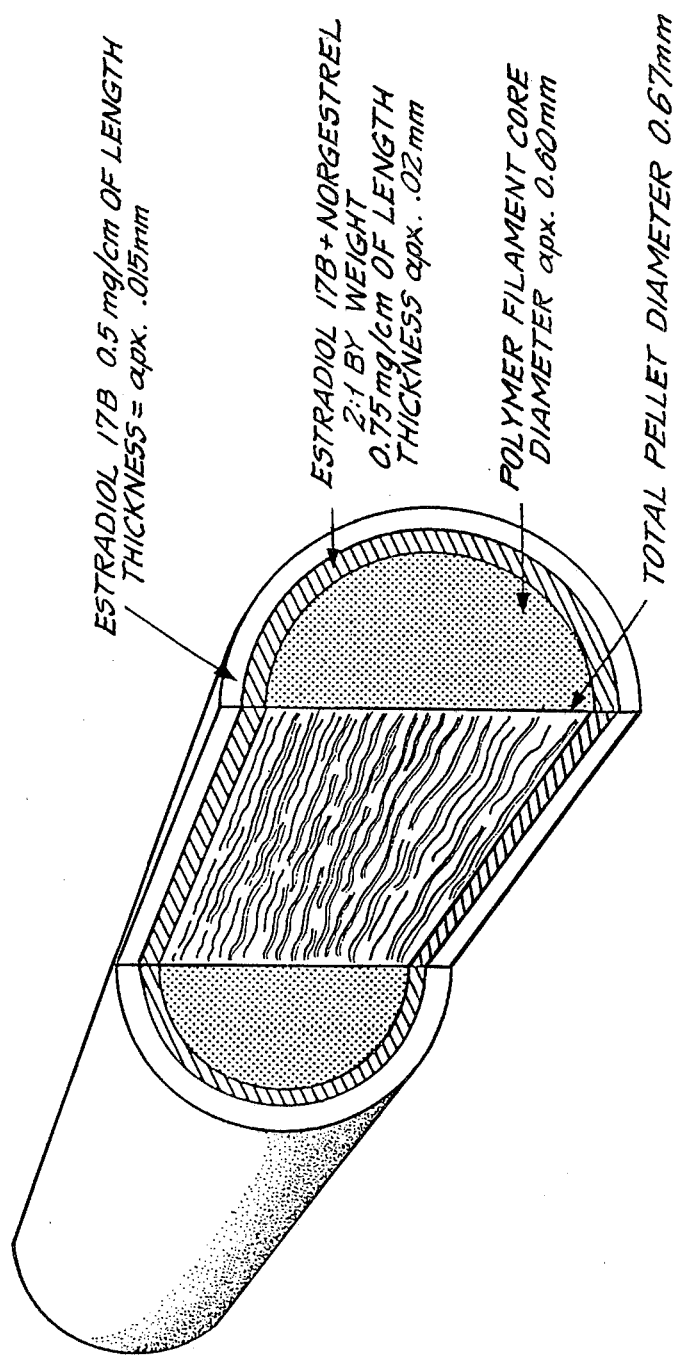
FIG. 8 is a similar schematic view showing a second alternate form of pellet.

In accordance with the invention, the device, generally indicated by reference character 10, comprises broadly: a guide element 11, and a disposable needle cartridge element 12 including a pellet element 13.

The guide element 11 is reusable, and is preferably formed of metallic construction. It includes a hollow elongated barrel 16, a first end 17 of which is provided with finger grips 18 on an outer surface 19. A removable (threaded) end wall or cap 20 includes a centrally disposed internally facing projection 21 forming an abutment, and first and second through openings 22 and 23. A second end 24 is partially closed by a wall 25 having a centrally disposed opening 26. Disposed within the barrel 16 is a slide member 30, a first end 31 having a manually engageable grip 32 supported on the end of first and second elongated arms 33 and 34 which pass through the openings 22 and 23, respectively. The opposite end of the arms 33 and 34 supports a cylinder 37 having a centrally disposed recess 38 and cartridge engaging means 39 which may be of luer or bayonet type for quick attachment. An alternate means (not shown) comprises a simple threaded interconnection.

The cartridge element 12 includes a hollow needle member 40 having a pointed tip 41, a second end 42 including a hub 43 having engagement means corresponding to the means 39. An obturator 44 includes a first end 45 which engages the abutment 21 and a second end 46 which extends into the base of the needle member 40 at 47.

The pellet element 15 contains 8 mg. of estradiol and is of diameter 0.6 mm. corresponding to the bore of the needle, and is 20 mm. in length. It may include a core of diameter approximating 0.2 mm. of progesterone/estradiol mixture to release progestin during the latter one third of the cycle, which core is then surrounded by a pure estradiol sleeve of outer diameter 0.4 mm. This size pellet element is calculated to provide normal physiologic levels of estradiol for three to four weeks before being completely absorbed. Adjustment of exact size and progesterone content may be necessary following appropriate experimentation.

Administration of the pellet will be apparent from a consideration of the drawings. To conveniently assemble the device, the threaded end wall 20 or cap may first be removed from the barrel 16 with its sliding arms 33-34 and cylinder-lock 37. The disposable cartridge 12 is then attached to the cylinder-lock 37 so that the obturator 44 passes through the cylinder and comes to rest with its free end 15 in the abutment 21 of the cap 20. The cartridge is then passed down the barrel 16 to emerge through the central opening 26 and the cap rethreaded into place on the barrel 16. FIG. 2 shows the assembled device 10 with the needle inserted into the subcutaneous fat of a patient. At this point, the pellet is positioned in the desired implant location, and the device is then removed by leaving the guide element 11 in the location shown, and while holding the barrel grips 18, the slide grip 32 is moved outwardly to result in withdrawing the needle member 40 while maintaining the obturator 44 in place. This results in uncovering the pellet, in situ in a progressive fashion until the slide member 30 has reached its outermost position, at which point the end 46 of the obturator has passed the free end of the needle. The pellet, at this point, is completely disengaged, and the device may be removed without difficulty.

For a completely disposable device as required, it is possible to eliminate the guide element, and place manually engageable means on a somewhat enlarged hub of the cartridge element which may be engaged between the index and third fingers of the hand, and the outer end of the obturator may be provided with thumb engaging means. In such case, index means is provided on the outer surface of the obturator to indicate when the needle member has been completely withdrawn.

As has been previously mentioned, the preferred configuration for the pellet includes a core of biologically inert biodegradable polymer, of the form illustrated in FIGS. 7 and 8 in the drawing. Shown in FIG. 7 is an estradiol pellet, cut diagramatically to shown both longitudinal and cross sections. In this pellet, the core is 0.60 mm. in diameter, and the estradiol layer is 0.025 mm. thick. FIG. 8 shows a similar pellet for sequential administration of first pure estradiol, then an estradiol-progestogen combination to simulate the normal menstrual cycle. Both pellets are designed to deliver about 100 micrograms of estradiol daily for approximately 21–23 days. The pellet shown in FIG. 8 delivers, in addition, about 50 micrograms per day of Norgestrel for the last 10–12 days of the cycle. Preliminary experiments suggest that the density of the estradiol layer will be about 2 mg./cubic mm. and that absorption rates will be satsifactory from a surface area of about 40–50 square mm. The pellet illustrated in FIG. 7 has an initial surface area of about 45 square mm. and a final surface area (at the end of absorption of the estradiol layer) of about 43 square mm. It contains approximately 2.2 mg. of estradiol.

Pellet fabrication may be made by a number of methods. The fiber core may be coated by dipping it in an estradiol melt and drawing it through a die while still hot to fix the outer diameter, by repeated dipping in a solution of estradiol and volatile solvent to build up a coat of the desired thickness, or by spray coating estradiol in a volatile solvent onto a rotating fiber with a fine spray under pressure. This is most conveniently done by feeding the core from a source of supply to a treatment area, and subsequently winding the treated core, after drying or solidifying upon a storage spindle. The pellets themselves can be of varying strength by varying the effective length thereof, individual pellets being cut from an elongated strand at desired intervals, preferably using automated equipment.

The present application also has application to the administration of pellets of a peptide contraceptive agent. LHRH (luliberin) is a 10 amino acid peptide (decapeptide) which is released from the hypothalamus and stimulates the pituitary gland to secret the gonadotropic glycoprotein hormones, luteinizing hormone (LH), and follicle stimulating hormone (FSH), which in turn regulate function of the ovary or testis, causing them to produce sex hormones and also eggs or sperm.

It has become evident from recent work that certain D-amino acid substituted analogues of LHRH can inhibit pituitary secretion of FSH and LH. Of particular interest are those analogues which exhibit potent LHRH antagonist activity and no antagonist activity. Since these peptides produce a hypogonadal state (i.e. the testes or ovaries become quiescent), which is reversible when the administration of the material ceases, they may have pharmacologic application in various medical conditions in which such a state is desirable. Such conditions include, for example, prostate cancer, breast cancer, female contraception, male contraception, endometriosis, and precocious puberty.

The above treatments are already known in the art. However, a suitable method for administration of these peptides to humans has not been found. They are easily destroyed in the gastrointestinal system, so no active oral preparation is likely to become available. A system for precise, long-term, metered, parenteral administration is highly desirable. Ideally, the injection would only be repeated weekly, monthly, or even less frequency. Since as little as 10 to 50 micrograms per day of these substances are likely to be effective, my disclosed coated cylindrical pellet in a fine needle cartridge would be ideal. There are relatively insoluble analogues (e.g. NAc-1Ala(1)-para chloro-dPhe (2)-dTryp(3,6) LHRH) whose characteristics have been published and which are in the art.

A suitable treatment would include the provision of a pellet coated with approximately 1.5 mg. of a water insoluble (lipophilic) analogue, with a surface area calculated to release approximately 50 micrograms per day for thirty days. When used for contraception, the normal sex steroid hormones must be supplied, since the analogue suppresses their production as well as the genesis of gametes. In women, this could be done by giving a sequential estrogen-progestogen pellet at the same time, and even in the same needle implantation as for the LHRH analogue pellet. In men, an alternative method for giving testosterone would have to be employed.

The advantages of this system for contraception would be the elimination of necessity to remember a daily pill, and the steroids are given only in physiologic doses, as compared with the large doses required for contraception, since the LHRH analogue is the actual contraceptive agent, and also parenterally, thus avoiding high dose steroid effects on the liver. This application would eliminate those toxic effects known to be associated with the birth control pill, such as hypertension, phlebitis, and embolism, increased risk of coronary disease, etc.

I wish it to be understood that I do not consider the invention limited to the precise details of structure shown and set forth in this specification, for obvious modifications will occur to those skilled in the art to which the invention pertains.

I claim:

1. A device for effecting the subcutaneous implacement of a solid pellet medicament comprising: an elongated rigid guide element including a first relatively fixed member and a second member slidably associated with said first member, said first member having manually engageable means and an abutment means thereon; said second member having first and second ends, manually engageable means located substantially at said first end, and cartridge engaging means on said second end; an elongated single use disposable cartridge including a hollow needle member having a first free end and a second end having a hub, said hub having an engaging means thereon corresponding to said cartridge engaging means on said second member, and selectively engaged therewith; an elongated medicament-containing pellet slidably positioned within said needle member, and an elongated obturator of a length greater than the length of said needle member, said obturator having a first end initially slidably positioned within said second end of said needle member, and a second end free of interconnection and abutting said abutment on said first member; whereby upon the subcutaneous insertion of said free end of said needle member, said pellet is positioned within the body of a patient; by movement of said second member in a given direction relative to said first member to withdraw said needle member, said obturator preventing movement of said pellet; said cartridge including said obturator being disposable after a single use.

2. A device in accordance with claim 1, further characterized in said first member having a hollow barrel, said second member, including a pair of arms terminating at first ends thereof in an annular grip, and at second ends thereof in a cylinder having said needle cartridge engaging means.

3. As a new article of manufacture, a single use disposable needle element for the subcutaneous implanting of medicament-containing pellets comprising: a hollow needle element having a first free end and a second end terminating in a hub; an elongated pellet of diameter corresponding to the inside diameter of said needle member and slidably disposed therein; and an obturator of effective length greater than the length of said needle member, and initially partially disposed within said needle member; whereby relative movement between said needle and said obturator at a given direction will eject said pellet; said hub having instrument engaging means thereon the engagement of which with an instrument immobilizes said obturator relative thereto.

* * * * *